United States Patent
Bueschken et al.

(10) Patent No.: US 7,632,961 B2
(45) Date of Patent: Dec. 15, 2009

(54) METHOD FOR THE PRODUCTION OF ALICYCLIC POLYCARBOXYLIC ACID ESTERS FROM PARTIAL ESTERS OF AROMATIC POLYCARBOXYLIC ACIDS

(75) Inventors: Wilfried Bueschken, Haltern (DE); Michael Grass, Haltern (DE); Alfred Kaizik, Marl (DE); Dietrich Maschmeyer, Recklinghausen (DE); Franz Nierlich, Marl (DE); Axel Tuchlenski, Muelheim (DE)

(73) Assignee: OXENO Olefinchemie GmbH, Marl (DE)

( * ) Notice: Subject to any disclaimer, the term of this patent is extended or adjusted under 35 U.S.C. 154(b) by 265 days.

(21) Appl. No.: 10/474,044

(22) PCT Filed: Sep. 14, 2002

(86) PCT No.: PCT/EP02/10332

§ 371 (c)(1),
(2), (4) Date: Oct. 15, 2003

(87) PCT Pub. No.: WO03/029179

PCT Pub. Date: Apr. 10, 2003

(65) Prior Publication Data

US 2005/0101800 A1    May 12, 2005

(30) Foreign Application Priority Data

Sep. 27, 2001 (DE) .............................. 101 47 776

(51) Int. Cl.
*C07C 69/74* (2006.01)
(52) U.S. Cl. .................................................... 560/127
(58) Field of Classification Search .................. 560/127
See application file for complete search history.

(56) References Cited

U.S. PATENT DOCUMENTS

| 2,070,770 | A | * | 2/1937 | Amend ....................... 560/127 |
| 5,536,856 | A | * | 7/1996 | Harrison et al. ............. 554/164 |
| 6,284,917 | B1 | * | 9/2001 | Brunner et al. ............. 560/127 |
| 2004/0097773 | A1 | | 5/2004 | Beckmann et al. |
| 2006/0036121 | A1 | | 2/2006 | Kaizik et al. |
| 2006/0167151 | A1 | | 7/2006 | Grass et al. |
| 2007/0060768 | A1 | | 3/2007 | Grass et al. |

FOREIGN PATENT DOCUMENTS

EP     0 005 737     12/1979

OTHER PUBLICATIONS

Nowakowski et al, Untersuchungen zur Synthese von Dibutylphthalat mia einem Kaytionne-Austauscher als katalysator, 1986, Chemie Ingenieur Technik, 58 (1), p. 48-49.*
Folmer et al, Generation of esters from carboxylic acids using Appel's salt (4,5-dichloro-1,2,3-dithiazolium chloride), 1993, Tetrahedron Letters, vol. 34, No. 17, pp. 2737-2740.*
U.S. Appl. No. 09/945,736, filed Sep. 5, 2001, Gubisch, et al.
U.S. Appl. No. 10/489,317, filed Mar. 18, 2004, Bueschken, et al.
U.S. Appl. No. 10/490,028, Mar. 19, 2004, Maschmeyer, et al.
U.S. Appl. No. 10/519,413, filed Jan. 6, 2005, Grass, et al.
U.S. Appl. No. 11/911,691, filed Oct. 16, 2007, Grass, et al.
U.S. Appl. No. 11/739,345, filed Apr. 24, 2007, Grass, et al.
U.S. Appl. No. 11/622,567, filed Jan. 12, 2007, Grass.

* cited by examiner

*Primary Examiner*—Taylor Victor Oh
(74) *Attorney, Agent, or Firm*—Oblon, Spivak, McClelland, Maier & Neustadt, L.L.P.

(57) ABSTRACT

The invention relates to a process for preparing full esters of alicyclic polycarboxylic acids from partial esters of aromatic polycarboxylic acids by hydrogenation of the partial ester followed by esterification of this compound.

12 Claims, No Drawings

METHOD FOR THE PRODUCTION OF ALICYCLIC POLYCARBOXYLIC ACID ESTERS FROM PARTIAL ESTERS OF AROMATIC POLYCARBOXYLIC ACIDS

The invention relates to a process for preparing full esters of alicyclic polycarboxylic acids from partial esters of aromatic polycarboxylic acids (by hydrogenation followed by esterification).

Cycloaliphatic polycarboxylic esters, such as the esters or cyclohexane-1,2-dicarboxylic acid, are used as a component in lubricating oils and as an auxiliary in metalworking. They are also used as plasticizers for polyolefins.

For plasticizing PVC, use is frequently made of esters of phthalic acid, for example the dibutyl, dioctyl, dinonyl, or didecyl ester. Since these phthalates are increasingly regarded as hazardous to health, it is likely that their use in plastics could be restricted. Cycloaliphatic polycarboxylic esters, some of which have been described in the literature as plasticizers for plastics, could then be available as replacements, even though their performance profile is somewhat different.

Alicyclic polycarboxylic esters may be obtained by esterifying the corresponding alicyclic polycarboxylic acids, or their anhydrides, or partial esters. Few of these compounds are available at low cost, since they have to be prepared in multistage syntheses.

For example, cyclohexane-1,2-dicarboxylic esters can be obtained via Diels-Alder reaction of butadiene with maleic anhydride, or with fumarates or maleics, followed by hydrogenation of the olefinic double bond in the cyclohexane derivative. If maleic anhydride is used as starting material, the synthesis also includes an esterification.

In many cases, alicyclic polycarboxylic esters are prepared by ring-hydrogenation of the corresponding aromatic polycarboxylic esters.

U.S. Pat. Nos. 5,286,898 and 5,319,129 describe processes which can hydrogenate dimethyl terephthalate on supported Pd catalysts treated with Ni, Pt and/or Ru, to give the corresponding dimethyl hexahydroterephthalate at temperatures of 140° C. or above and at a pressure of from 50 to 170 bar. DE 28 23 165 discloses a process for the hydrogenation of aromatic carboxylic esters on supported Ni, Ru, Rh, and/or Pd catalysts, to give the corresponding cycloaliphatic carboxylic esters, at from 70 to 250° C. and from 30 to 200 bar. U.S. Pat. No. 3,027,398 describes the hydrogenation of dimethyl terephthalate on supported Ru catalysts at from 110 to 140° C. and from 35 to 105 bar.

DE 197 56 913 and WO 99/32427 disclose a process for the hydrogenation of benzene polycarboxylic esters to give the corresponding cycloaliphatic compounds. Here, use is made of supported catalysts which comprise Ru on its own or together with at least one metal of the $1^{st}$, $7^{th}$ or $8^{th}$ transition group of the periodic table, and have 50% of macropores.

The aromatic carboxylic esters used for the ring hydrogenation process are mostly prepared by esterifying the corresponding carboxylic acids or their anhydrides, the corresponding partial esters being produced as an intermediate in the reaction mixture. To reach full esterification here, relatively long reaction times and/or relatively drastic reaction conditions may be needed.

The processes described in the abovementioned literature for the preparation of cycloaliphatic polycarboxylic esters are therefore based on the following sequence of reactions:

1. Preparation of an aromatic polycarboxylic ester, a partial ester generally being formed first and reacted to give the full ester
2. Purification and work-up of the resultant polycarboxylic ester to give the pure product
3. Hydrogenation of the aromatic polycarboxylic ester to give the corresponding cycloaliphatic polycarboxylic ester
4. Optionally: purification and work-up of the resultant cycloaliphatic polycarboxylic ester to give the pure product.

There are also conceivable versions of the process in which unpurified crude ester is hydrogenated. However, a disadvantage of these processes is that the activity of the hydrogenation catalyst is reduced by deposits deriving from the esterification catalyst, the result being a requirement for frequent catalyst change and a resultant fall in cost-effectiveness.

Since catalysis of the esterification reaction is generally homogeneous, the crude product of the esterification has to be freed from catalysts, by-products, and alcohol prior to its hydrogenation, i.e. has to be worked up. This work-up is complicated, since the commonly used processes have two purification stages, and there can therefore be two yield losses.

An object is therefore to provide a simpler and more cost-effective process for the preparation of alicyclic polycarboxylic esters.

Surprisingly, it is possible to obtain cycloaliphatic polycarboxylic esters in a simple and cost-effective manner by hydrogenation of an aromatic partial ester of an aromatic polycarboxylic acid or of a mixture which comprises one or more partial esters of one or more aromatic polycarboxylic acids, followed by esterification of the resultant cycloaliphatic polycarboxylic partial ester.

The present invention therefore provides a process for the preparation of cycloaliphatic polycarboxylic esters, which comprises a) hydrogenating a partial ester of the corresponding aromatic polycarboxylic acid or of the corresponding aromatic polycarboxylic anhydride, and
b) reacting the resultant cycloaliphatic partial ester with an alcohol to give the full ester.

The full esters may optionally be purified by filtration, steam distillation, or stripping with steam.

Starting materials which may be used in the process of the invention are pure substances, e.g. compounds which are isomerically pure with respect to the ester side chain, or else mixtures of isomers, or indeed mixtures of different esters, both with respect to the chain length of the ester group and with respect to the aromatic system.

One way in which mixtures of isomers with respect to the ester side chain are produced is, for example, during the preparation of phthalate esters of isononanol, which is a $C_9$ isomer mixture. It is also possible to use a mixture of $C_8$ and $C_9$ phthalate partial esters and/or an isomeric mixture of 1,2- and 1,4-phthalate partial esters. Partial esters of phthalic acid are its monoesters with one remaining carboxylic acid function.

In one particular embodiment of the process of the invention, a partial ester is first prepared from an aromatic polycarboxylic acid or the corresponding anhydride and an alcohol or alcohol mixture. Processes for esterification of carboxylic acids or their anhydrides are known to the skilled worker. In the esterification of polycarboxylic acids, and in particular of their anhydrides, partial esters are first produced, i.e. the esterification reaction does not proceed as far as the fully esterified polycarboxylic ester. For example, in the esterification reaction of phthalic anhydride with alcohols, the corresponding monoester is first formed at an elevated temperature by an autocatalytic mechanism. However, if the corresponding diester is desired it is advantageous to carry out the second esterification stage at a higher temperature and/or with addition of a catalyst.

For the purposes of the present invention, partial esters are compounds which, besides at least one ester function, also contain at least one free carboxylic acid function or anhydride function. One advantage of the process of the invention is that in both steps of the process it is possible to exert influence on the cis/trans ratio of the alicyclic polycarboxylic acid derivatives, so that products with different trans contents can be obtained. Products obtained by the process of the invention can have a higher trans content than those obtained in direct hydrogenation of the corresponding aromatic polycarboxylic ester. Cis and trans compounds perform differently. The use of trans-rich products as plasticizers for plastics is advisable if, for example, the plasticizer is required to have relatively low volatility.

A further advantage is that only one purification stage, which may be composed of two or more substeps, is needed to prepare the alicyclic polycarboxylic ester by the process of the invention.

The catalysts used in the process of the invention for the hydrogenation of the partial esters are in most cases the same as those known from the literature for the hydrogenation of aromatic full esters to give the corresponding cycloaliphatic full esters.

These are mostly supported catalysts. The active metal present in them may in principle be any of the metals of the $8^{th}$ group of the periodic table. The active metals present in them are preferably platinum, rhodium, palladium, cobalt, nickel or ruthenium, or a mixture of two or more of these. Other active metals may be elements of the first or seventh transition group of the periodic table, for example copper, rhenium, or a combination of these.

The support materials for the hydrogenation catalysts may be: activated carbon, aluminum oxide, alumosilicate, silicon dioxide, titanium dioxide, zirconium dioxide, magnesium oxide, zinc oxide, or a mixture of these.

Examples of a material which may be used in the process of the invention are ruthenium/aluminum oxide catalysts of types H14163 or B4168/10r from Degussa AG, Dusseldorf, Germany.

The catalysts used in the process of the invention for the hydrogenation of the aromatic partial esters may be prepared by applying at least one metal of the $8^{th}$ transition group of the periodic table to a suitable support.

The application may be achieved by saturating the support in aqueous metal salt solutions, by spraying appropriate metal salt solutions onto the support, or by other suitable methods. Suitable salts of metals of the $8^{th}$ transition group of the periodic table are the nitrates, nitrosyl nitrates, halides, carbonates, carboxylates, acetylacetonates, chloro complexes, nitrito complexes, or amine complexes of the corresponding metals.

The supports coated or saturated with the metal salt solution are then dried, preferably at temperatures of from 100 to 150° C., and calcined if desired at temperatures of 200 to 600° C., preferably from 350 to 450° C.

The coated and dried and, if desired, calcined supports are then activated by treatment with a stream of gas which comprises free hydrogen, and at temperatures from 30 to 600° C., preferably from 100 to 450° C. The stream of gas is preferably composed of a mixture of hydrogen and nitrogen. It can be advantageous to increase the hydrogen content during the course of the activation. For example, the hydrogen content in the gas mixture may be 10% at the start of the activation and over 90% at the end of the activation process.

Where appropriate, this activation may be carried out in the same reactor in which the partial ester is hydrogenated. The activation of the catalyst may optionally be undertaken in the presence of a liquid phase which trickles over the catalyst.

The amount of the metal salt solution or metal solutions applied to the support is such that the total content of active metal, based in each case on the total weight of the catalyst, is from 0.01 to 30% by weight, preferably from 0.01 to 5% by weight, very particularly from 0.05 to 2% by weight.

The surface area of metal on the catalysts is from 1 to 50 $m^2/g$. The surface area of the metal is determined by the chemisorption method described by J. Lemaitre et al. "characterization of Heterogeneous Catalysts", Ed. Francis Delanney, Marcel Dekker, New York 1984, pp. 310-324.

The support materials for the catalysts may be macroporous, mesoporous, or microporous, or have pores, various numbers of which fall into the three ranges mentioned. Their BET surface area is from 5 to 600 $m^2/g$.

The hydrogenation in the process of the invention is preferably carried out in the liquid phase. The hydrogenation may be carried out continuously or batchwise on suspended catalysts or on particulate catalysts in a fixed bed. In the process of the invention, preference is given to continuous hydrogenation on a fixed-bed arrangement of catalysts where the products/starting material phase is primarily in the liquid state under the conditions of the reaction.

Various versions of the process of the invention may be selected. It may be carried out adiabatically or practically isothermally, i.e. with a temperature rise typically smaller than 10° C., in one or more stages. In the latter case, all of the reactors, advantageously tubular reactors, may be operated adiabatically or practically isothermally, or else one or more may be operated adiabatically and the others practically isothermally. It is moreover possible to hydrogenate the aromatic polyesters in a straight pass or with product return.

The process of the invention is carried out in the liquid/gas mixed phase or liquid phase in cocurrent mode in three-phase reactors, the hydrogenating gas being distributed in the liquid starting material/product stream in a manner known per se. In the interests of uniform liquid distribution, of improved dissipation of the heat of reaction, and of high space-time yield, the reactors are preferably operated with high liquid flow rates of 15 to 120, in particular from 25 to 80, $m^3$ per $m^2$ of cross section of the empty reactor per hour. If a reactor is operated with a straight pass, the liquid hourly space velocity (LHSV) over the catalyst may be from 0.1 to 10 $h^{-1}$.

The hydrogenation may be carried out in the absence, or preferably in the presence, of a solvent. Solvents which may be used are any of the liquids which form a homogenous solution with the starting material and product, have inert behavior under hydrogenation conditions, and are easy to remove from the product. The solvent may also be a mixture of two or more substances and, where appropriate, comprise water.

Examples of substances which may be used as solvents are the following: Straight-chain or cyclic esters, such as tetrahydrofuran or dioxane, and also aliphatic alcohols whose alkyl radical has from 1 to 13 carbon atoms.

Examples of alcohols which may preferably be used are isopropanol, n-butanol, isobutanol, n-pentanol, 2-ethylhexanol, nonanols, industrial nanonaol mixtures, decanol, and industrial decanol mixtures.

If alcohol is used as solvent it can be advantageous to use the alcohol or alcohol mixture which would be produced during saponification of the product (e.g. isononanol as solvent in the hydrogenation of monoisononyl phthalate). This prevents any by-product formation via transesterification. Another preferred solvent is the hydrogenation product itself.

By using a solvent it is possible to limit the concentration of aromatic compounds in the reactor feed, and the result can be better temperature control achieved in the reactor. This can minimize side-reactions and therefore increase the yield of product. The content of aromatic compounds in the reactor feed is preferably from 1 to 35%, in particular from 5 to 25%. The desired concentration range can be adjusted via the circulation rate (quantitative ratio of returned hydrogenation discharge to starting material) in the case of reactors operated in loop mode.

The hydrogenation in the process of the invention is carried out in the pressure range from 5 to 300 bar, in particular from 15 to 220 bar, very particularly from 50 to 200 bar. The hydrogenation temperatures are from 50 to 200° C., in particular from 80 to 160° C.

Hydrogenation gases which may be used are any desired hydrogen-containing gas mixtures in which there are no detrimental amounts present of catalyst poisons, such as carbon monoxide or hydrogen sulfide. Examples of the inert gas constituents are nitrogen and methane. It is preferable to use hydrogen at a purity greater than 95%, in particular greater than 98%.

The aromatic polycarboxylic acids and, respectively, their corresponding anhydrides preferably used in the process of the invention contain 2, 3 or 4 carboxyl functions. Examples of compounds of this type are phthalate acid and trimellitic acid.

The aromatic polycarboxylic acids and, respectively, the corresponding polycarboxylic anhydrides preferably contain from 1 to 5 fused benzene rings or other annellated radicals. Examples of fused-on benzene rings are benzene systems, biphenyl systems, naphthalene systems, anthracene systems, and phenanthrene systems.

Particularly preferred partial esters of the aromatic polycarboxylic acid are the monoesters of 1,2-, 1,3- or 1,4-phthalate acid, (or their anhydride), and the mono- or di-esters of 1,2,3-, 1,2,4-, or 1,3,5-trimellitic acid.

It is preferable for a monoisononyl phthalate or a monooctyl phthalate or a monodecyl phthalate to be reacted in the process of the invention to give the corresponding cyclohexanedicarboxylic esters.

The process of the invention can use partial esters of the following aromatic acids:
naphthalene-1,2-dicarboxylic acid, naphthalene-1,3-dicarboxylic acid, naphthalene-1,4-dicarboxylic acid, naphthalene-1,5-dicarboxylic acid, naphthalene-1,6-dicarboxylic acid, naphthalene-1,7-dicarboxylic acid, naphthalene-1,8-dicarboxylic acid, phthalic acid, isophthalic acid, terephthalic acid, benzene-1,2,3-tricarboxylic acid, benzene-1,2,4-tricarboxylic acid (trimellitic acid), benzene-1,3,5-tricarboxylic acid (trimesinic acid), benzene-1,2,3,4-tetracarboxylic acid, benzene-1,2,4,5-tetracarboxylic acid (pyromellitic acid). It is also possible to use acids produced from the acids mentioned through substitution of one or more hydrogen atoms on the aromatic ring by alkyl, cycloalkyl, or alkoxyalkyl groups. It is also possible to use polycarboxylic acids having an anthracene skeleton, phenanthrene skeleton, or diphenyl oxide skeleton.

The alcohol components of the partial and full esters may be branched or unbranched alkyl, cycloalkyl, or alkoxyalkyl groups having from 1 to 25, in particular from 3 to 15, very particularly from 8 to 13, carbon atoms.

It is possible to use alcohol mixtures and, respectively, partial ester mixtures with various alcohols. Mixtures may be either alcohols of different chain length or isomeric mixtures of alcohols of the same chain length.

The process of the invention can also use mixtures which comprise at least two partial esters. Examples of starting materials of this type may be: Mixtures produced from tribasic carboxylic acids by partial esterification. Monoalkyl and dialkyl esters may be present alongside one another in these mixtures.

A mixture with at least two partial esters is produced during partial esterification of a polycarboxylic acid with an alcohol mixture.

Another way in which mixtures of partial esters can be produced is via reaction of a mixture of at least two polycarboxylic acids with an alcohol or alcohol mixture.

Low-cost alcohol mixtures are frequently used for esterification in industry.

Examples of these are $C_5$ alcohol mixtures, prepared from linear butenes by hydroformylation followed by hydrogenation;

$C_5$ alcohol mixtures prepared from butene mixtures which comprise linear butenes and isobutene, by hydroformylation followed by hydrogenation;

$C_6$ alcohol mixtures prepared from a pentene or from a mixture of two or more pentenes, by hydroformylation followed by hydrogenation;

$C_7$ alcohol mixtures prepared from triethylene or dipropene or from a hexane isomer, or from some other mixture of hexane isomers, by hydroformylation followed by hydrogenation;

2-ethylhexanol (2 isomers), prepared by aldol condensation of n-butyraldehyde followed by hydrogenation;

$C_9$ alcohol mixtures prepared from $C_4$ olefins by dimerization, hydroformylation and hydrogenation. The starting materials here may be isobutene or a mixture of linear butenes, or mixtures with linear butenes and isobutene. The $C_4$ olefins may be dimerized with the aid of various catalysts, such as protonic acids, zeolites, organometallic nickel compounds, or solid nickel-containing catalysts. The $C_8$ olefin mixtures may be hydroformylated with the aid of rhodium catalysts or cobalt catalysts. There is therefore a wide variety of industrial $C_9$ alcohol mixtures. $C_{10}$ alcohol mixtures prepared by tripropylene, by hydroformylation followed by hydrogenation;

2-propylheptanol (2 isomers), prepared by aldol condensation of valeraldehyde followed by hydrogenation;

$C_{10}$ alcohol mixtures prepared from a mixture of at least two $C_5$ aldehydes by aldol condensation followed by hydrogenation;

$C_{13}$ alcohol mixtures prepared from hexaethylene, tetrapropylene, or tributene, by hydroformylation followed by hydrogenation.

Other alcohol mixtures may be obtained by hydroformylation followed by hydrogenation from olefins or olefin mixtures which are produced, for example, in Fischer-Tropsch syntheses, in dehydrogenation processes on hydrocarbons, in metathesis reactions, in the polygas process, or in other industrial processes.

It is moreover possible to use olefin mixtures with olefins of varying C numbers for preparing alcohol mixtures.

The process of the invention can use any of the partial ester mixtures prepared from aromatic polycarboxylic acids and the above-mentioned alcohol mixtures. According to the invention, preference is given to esters prepared from phthalic acid or phthalic anhydride and from an alcohol or mixture of isomeric alcohols having from 1 to 25 carbon atoms.

The partial esters used may be in the form of isomerically pure esters or of a mixture of isomeric partial esters, or of a mixture of various non-isomeric partial esters, or preferably of a reaction mixture produced during preparation of partial esters, where appropriate after catalyst removal.

The partial esters used in the process of the invention may be pure substances or industrial mixtures, e.g. from the esterification reaction. Examples of compounds present in mixtures of this type, besides the partial ester, are, for example, full esters, polycarboxylic acid/polycarboxylic anhydride (in each case from 0 to 15 mol %, based on the partial ester), alcohol, water, and/or the esterification catalyst.

Aromatic polycarboxylic acids or their anhydrides and alcohols (alcohol mixtures) may optionally be fed into the hydrogenation stage in the intended ratio, separately or together. For example, phthalic anhydride and alcohol (alcohol mixture) may be fed into the outer loop of a hydrogenation reactor operated in loop mode. Partial ester formation occurs here primarily in the outer loop.

The partial esterification of the aromatic polycarboxylic acids may be carried out by known processes without catalysis or with catalysis by Lewis or Brönstedt acids or metal compounds.

Preparation of partial esters from anhydrides of aromatic polycarboxylic acids generally needs no catalyst. For example, phthalic anhydride reacts with alcohols in the temperature range from 110 to 160° C. very quickly to give the corresponding partial esters. The reaction of an anhydride of an aromatic carboxylic acid may be carried out with an excess of alcohol. Very small amounts of full ester may be present in the partial ester mixture. Since the hydrogenation-discharge is in all cases esterified, it is advantageous for the amount of excess alcohol used in the partial ester preparation to be already that intended for the esterification stage which follows the hydrogenation.

Besides the alicyclic partial ester(s), the product-discharges from the hydrogenation may comprise full esters and alicyclic polycarboxylic acids, alcohol, and also solvents, by-products, and water.

These mixtures are preferably reacted to give the full esters by methods known per se, without further purification. This post-esterification may take place by an autocatalytic or catalytic mechanism, for example using Brönstedt or Lewis acids. Quite irrespective of the type of catalysis selected, the result is always a temperature-dependent equilibrium between the starting materials (partial ester and, where appropriate, carboxylic acid and alcohol) and the products (esters and water). In order to shift the equilibrium in favor of the full ester, use may be made of entrainer with the aid of which the water of the reaction can be removed from the mixture. Since the alcohols used for the esterification have lower boiling points than the polycarboxylic acid, and its partial esters, and its full esters, and are not fully miscible with water, they are used as entrainer, which can be returned to the process after water removal.

The alcohol or alcohol mixture used to form the full ester and simultaneously serving as entrainer is used in excess, this preferably being from 5 to 50%, in particular from 10 to 30%, of the amount needed to form the full ester from the polycarboxylic acid.

Esterification catalysts which may be used are acids, such as sulfuric acid, methanesulfonic acid, or p-toluenesulfonic acid, or metals or compounds of these. Examples of those suitable are tin, titanium, zirconium, which may be used as finely divided metals or advantageously in the form of their salts, or of the oxides or, of the soluble organic compounds. Unlike protic acids, the metal catalysts are high-temperature catalysts which achieve their full activity only at temperatures above 180° C. However, their use is preferred since the amount of by-products which they form, for example olefins from the alcohol used, is smaller than with protic catalysis. Examples of metal catalysts are tin powder, tin (II) oxide, tin (II) oxalate, titanium esters, such as tetraisopropyl orthotitanate or tetrabutyl orthotitanate, and also zirconium esters, such as tetrabutyl zirconate.

The alcohol or alcohol mixture used during the full esterification of the cycloaliphatic partial ester may be the same as that which would be produced or is produced during saponification of the partial ester of the aromatic polycarboxylic acid.

In one preferred embodiment of the invention, the partial ester is first prepared, e.g. as in the patent literature cited.

The alcohol or alcohol mixture used in the full esterification in step b) of the process of the invention may then be the same as that which was used to prepare the partial ester.

It is also possible for another alcohol or another alcohol mixture to be used during the esterification in step b) of the process of the invention. For example, it is possible to hydrogenate a partial ester having a $C_8$ alcohol component and to react this compound with a $C_9$ alcohol component to give the full ester.

The catalyst concentration depends on the nature of the catalyst. For the titanium compounds whose use is preferred it is from 0.005 to 1.0% by weight based on the reaction mixture, in particular from 0.01 to 0.5% by weight, very particularly from 0.01 to 0.1% by weight.

When titanium catalysts are used, their reaction temperatures are from 160 to 270° C., preferably from 180 to 250° C. The ideal temperatures depend on the starting materials, the progress of the reaction, and the catalyst concentration. They may easily be determined by trials for each particular case. Higher temperatures increase the reaction rates and favor side-reactions, such as elimination of water from alcohols or the formation of colored by-products. For removal of the water of the reaction it is useful that the alcohol can be removed from the reaction mixture by distillation. The desired temperature or the desired temperature range may be set via the pressure in the reaction vessel. In the case of low-boiling alcohols, therefore, the reaction is carried out at superatmospheric pressure, and in the case of higher-boiling alcohols it is carried out at subatmospheric pressure. For example, the operating temperature range during the reaction of phthalic anhydride with a mixture of isomeric nonanoles is from 170 to 250° C. in the pressure range from 1 bar to 10 m bar.

The liquid to be returned to the reaction may be composed to some extent or entirely of alcohol, which is obtained by work-up of the azeotropic distillate. It is also possible for the work-up to be carried out at a later juncture and for the liquid removed to be replaced entirely or to some extent by fresh alcohol, i.e. from alcohol provided in a feed vessel.

The crude ester mixtures, which besides the full ester(s) comprise alcohol, very small amounts of partial ester, catalyst or its downstream products, and, where appropriate, by-products, are worked up by methods known per se. This work-up encompasses the following steps: removal of the excess alcohol and, where appropriate, low boilers, optionally including steam distillation, neutralization of the acids present, conversion of the catalyst into a residue capable of easy filtration, removal of the solids, and, where appropriate, drying. The sequence of these steps can differ, depending on the work-up methods used.

Work-up methods for crude ester mixtures are described by way of example in DE 197 21 347 C2.

The present invention further provides the use of the alicyclic polycarboxylic esters prepared according to the invention as plasticizers in plastics. Preferred plastics are PVC, and homo- and copolymers based on ethylene, on propylene, on vinyl acetate, on glycidyl acrylate, on glycidyl methacrylate, on acrylates, or on acrylates having branched or unbranched alkyl radicals bonded to the oxygen atom of the ester group and having from one to ten carbon atoms, or on styrene or on acryinitrile, and homo- or copolymers of cyclic olefins.

The following plastics may be mentioned as representatives of the above groups:

Polyacrylates having identical or different alkyl radicals having from 4 to 8 carbon atoms, bonded to the oxygen atom of the ester group, in particular having the n-butyl, n-hexyl, n-octyl, or 2-ethylhexyl radical, polymethacrylate, polymethyl methacrylate, methyl acrylate-butyl acrylate copolymers, methyl methacrylate-butyl methacrylate copolymers, ethylene-vinyl acetate copolymers, chlorinated polyethylene, nitrile rubber, acrylnitrile-butadiene-styrene copolymers, ethylene-propylene copolymers, ethylene-propylene-diene copolymers, styrene-acrylnitrile copolymers, acryinitrile-butadiene rubber, styrene-butadiene elastomers, and methyl methacrylate-styrene-butadiene copolymers.

The alicyclic polycarboxylic esters of the invention may moreover be used to modify plastics mixtures, for example the mixture of a polyolefin with a polyamide.

Mixtures made from plastics and the alicyclic polycarboxylic esters of the invention or the polycarboxylic esters prepared according to the invention are also provided by the present invention. Suitable plastics are the abovementioned compounds. Mixtures of this type preferably comprise at least 5% by weight, particularly preferably from 20 to 80% by weight, very particularly preferably from 30 to 70% by weight, of the alicyclic polycarboxylic esters.

Mixtures made from plastics, in particular PVC, and comprising one or more of the alicyclic polycarboxylic esters of the invention may be present in the following products, for example:

casings for electrical devices, such as kitchen machines, computer cases, casings and components of phonographic and television equipment, of piping, of apparatus, of cables, of wire sheathing, of insulating tapes, of window profiles, in interior decoration, in vehicle construction and furniture construction, plastosols, in floor coverings, medical products, packaging for food or drink, gaskets, films, composite films, phonographic disks, synthetic leather, toys, containers for packaging, adhesive-tape films, clothing, coatings, and fibers for fabrics.

Mixtures made from plastic, in particular PVC, and comprising one or more of the alicyclic polycarboxylic esters of the invention may moreover be used for producing the following products, for example:

a casing for electrical devices, piping, apparatus, a cable, wire sheathing, a window profile, a floor covering, a medical product, a toy, packaging for food or drink, a gasket, a film, a composite film, a phonographic disk, synthetic leather, a container for packaging, an adhesive-tape film, clothing, a coating, or a fiber for fabrics.

Besides the abovementioned applications, the alicyclic polycarboxylic esters of the invention may be used as a component in lubricating oil, as a constituent of coolants, or as metal working liquids.

The examples below are intended to illustrate the invention without limiting its scope of protection, as given in the description and the claims.

EXAMPLE 1

Hydrogenation of Diisononyl Phthalate (Vestinol 9)

Comparative Example 590 g of Vestinol 9 are hydrogenated using pure hydrogen in the presence of the ruthenium catalyst B4168/10r in a 600 ml pressure reactor at a pressure of 200 bar and at a temperature of 120° C. Once hydrogen uptake has ended, the reactor was depressurized and the product was analyzed. Diisononyl phthalate conversion was then 99.9%. The yield of di(isononyl) cyclohexane-1,2-dicarboxylate was 99.8%, and a cis/trans ratio determined by means of $^1$H NMR spectroscopy was 97:3.

| | |
|---|---|
| Measurement device: | Avance DPX-360 NMR spectrometer from the company Bruker |
| Measurement frequency: | 360 MHz |
| Sample head: | QNP sample head, 5 mm |
| Solvent: | CDCl$_3$ (degree of deuteration 99.8%) Tetramethylsilane (TMS) |
| Standard: | 303 K |
| Measurement temperature: | 32 |
| Number of scans: | 1 s |
| Delay: | 4.4 s |
| Acquisition time: | 7440.5 Hz |
| Spectral width: | 30° |
| Pulse angle: | 3.2 μs. |
| Pulse length: | |

An example of the method of recording the $^1$H NMR spectra comprised dissolving about 20 mg of the sample in about 0.6 ml of CDCl$_3$ (with 1% weight of TMS). The spectra were recorded under the conditions given above and referenced to TMS=0 ppm.

In the $^1$H NMR spectra obtained, the methyne signals for cis- and trans-dialkyl hexahydrophthalates could be distinguished with chemical shifts of about 2.8 ppm and 2.6 ppm, respectively. The signal shifted toward lower field corresponding to the cis compound (larger ppm value). To quantify the isomer, the integrals were determined from 3.0 ppm to 2.8(2) ppm and from 2.7(2) ppm to 2.5 ppm, the two integrals being separated in the middle between the signals. The ratio of the two isomeric structures could be determined from the intensity ratios.

EXAMPLE 2

Synthesis of Monoisononyl Phthalate 444 g of phthalate anhydride (3 mol) and 432 g of isononanol (3 mol) (precursor of Vestinol 9) were heated slowly in a round-bottomed flask which had internal thermometer and stirrer and on which a reflux condenser had been placed. Monoester formation started at a temperature of 117° C. and was discernible via a marked rise in temperature. Immediately after the temperature rise, the supply of heat was interrupted. After about 10 minutes the mixture, which had now reached its final temperature of about 150° C., was cooled. The hydrogenation proceeds quantitatively.

Gas chromatography permitted a composition to be determined at about 95% by weight of monoester, 3% by weight of diester, 0.5% by weight of isononanol and 1.5% by weight of phthalic acid.

EXAMPLE 3

Hydrogenation of Monoisononyl Phthalate 487 g (1.67 mol) of the monoester mixture prepared in example 2 were mixed, without further work-up, with 240 g (1.67 mol) of isononanol (precursor of Vestinol 9), and charged to a 1000 ml reactor under nitrogen. 74 g of the ruthenium catalyst B4168/10r were added and hydrogenation with hydrogen was carried out at 200 bar and 120° C. Once the ring-hydrogenation of the aromatic carboxylic derivatives had ended, the reactor was depressurized.

EXAMPLE 4

Esterification of the Ring-Hydrogenated Monoester to Give the Diester

The reactor discharge from example 3 was transferred to a standard esterification apparatus and mixed with a further 120 g (0.83 mol) of isononanol and about 0.07 g of tetrabutyl titanate. Toluene was used as entrainer, and its amount in the reaction mixture was effective in keeping the esterification temperature constant at 180° C. The esterification proceeded with reflux of the alcohol and toluene charge at atmospheric pressure, and the water produced was taken off at the water separator. Esterification was carried out as far as an acid value of <0.5 mg KOH/g. The alcohol was distilled off at a Claisen bridge at this temperature until the final pressure of 10 mbar had been reached. The mixture was then cooled to 80° C. and neutralized dropwise with 10% strength aqueous sodium hydroxide solution, and subsequently stirred for approximately 30 further minutes.

The ester was then heated to 180° C. in a 10 mbar vacuum. Distilled or demineralized water (8%, based on the initial weight of crude ester) was then added dropwise at constant temperature via the immersion tube. Once the work-up had ended, the heating was switched off. The product then cooled in vacuo to 80° C. and was then filtered through a suction-type filter funnel, using filter paper and filtration aid, to give a clear filtrate.

The ratio of cis- and trans-cyclohexane-1,2-dicarboxylic diesters was determined by $^1$H NMR spectroscopy (see above). It was 51 to 49.

EXAMPLE 5

Esterification of the Ring-Hydrogenated Monoester to Give the Diester

The esterification of the product discharged from the reaction in example 3 was carried out in a manner similar to example 4, except that no toluene was added. This resulted in a rise in the esterification temperature to 250° C.

After work-up, investigation of the product by $^1$H NMR spectroscopy gave a cis/trans ratio of about 21/79.

Examples 4 and 5 show that products with different trans contents for the cyclohexane-1,2-dicarboxylic esters can be prepared by varying the esterification conditions.

The process of the invention results in higher trans contents than the hydrogenation of Vestinol 9 (comparative example 1), using the same hydrogenation conditions during the hydrogenation of the monoester and of the diester.

What is claimed is:

1. A process for preparing cycloaliphatic polycarboxylic esters, which comprises:
    a) hydrogenating a partial ester of the corresponding aromatic polycarboxylic acid or of the corresponding aromatic polycarboxylic anhydride whose carboxylic acid or anhydride groups have been partially esterified with at least one branched or unbranched alkyl, cycloalkyl, and/or alkoxyalkyl alcohol having from 3 to 15 carbon atoms, and
    b) reacting the resultant cycloaliphatic partial ester with at least one branched or unbranched alkyl, cycloalkyl, and/or alkoxyalkyl alcohol having from 3 to 15 carbon atoms in the presence of a titanium or zirconium catalyst to give a full ester product.
2. The process as claimed in claim 1, wherein
    the hydrogenation of the aromatic partial ester is carried out with a catalyst comprising at least one metal of the $8^{th}$ transition group of the periodic table.
3. The process as claimed in claim 1, wherein
    the alcohol or alcohol mixture reacted with the cycloaliphatic partial ester is the same as that which would be obtained by saponifying the partial ester of the aromatic polycarboxylic acid.
4. The process as claimed in claim 1, wherein
    the alcohol or alcohol mixture reacted with the cycloaliphatic partial ester is other than that which would be obtained by saponifying the partial ester of the aromatic polycarboxylic acid.
5. The process as claimed in claim 1, wherein the aromatic polycarboxylic acid or the corresponding polycarboxylic anhydride comprises 2, 3 or 4 carboxyl functional groups.
6. The process as claimed in claim 1, wherein the aromatic polycarboxylic acid or the corresponding polycarboxylic anhydride is comprised of one benzene ring or from 2 to 5 condensed benzene rings.
7. The process as claimed in claim 1, wherein the alcohol comprises branched or unbranched alkyl, cycloalkyl, and/or alkoxyalkyl groups having from 8 to 13 carbon atoms.
8. The process as claimed in claim 1, wherein the partial ester is a partial ester of an aromatic polycarboxylic acid and comprises a monoester of a benzene-1,2-, 1,3-, or 1,4-dicarboxylic acid.
9. The process as claimed in claim 1, wherein the partial ester is a partial ester of an aromatic polycarboxylic acid and is a mono- or diester of 1,2,3-, 1,2-4- or 1,3,5-trimellitic acid.
10. The process as claimed in claim 2, wherein the alcohol or alcohol mixture reacted with the cycloaliphatic partial ester is the same as that which would be obtained by saponifying the partial ester of the aromatic polycarboxylic acid.
11. The process as claimed in claim 2, wherein the alcohol or alcohol mixture reacted with the cycloaliphatic partial ester is other than that which would be obtained by saponifying the partial ester of the aromatic polycarboxylic acid.
12. The process as claimed in claim 1, wherein the alcohol component of the cycloaliphatic partial ester is a $C_8$ or $C_9$ aliphatic alcohol or isomer mixture of these alcohols and alcohol reactant of step (b) is a $C_8$ or $C_9$ aliphatic alcohol or isomer mixture of these alcohols.

* * * * *